(12) United States Patent
Cheng et al.

(10) Patent No.: US 10,478,058 B2
(45) Date of Patent: Nov. 19, 2019

(54) SPECKLE REDUCTION IN OPTICAL COHERENCE TOMOGRAPHY IMAGES

(71) Applicants: AGENCY FOR SCIENCE, TECHNOLOGY AND RESEARCH, Singapore (SG); KABUSHIKI KAISHA TOPCON, Tokyo (JP)

(72) Inventors: Jun Cheng, Singapore (SG); Jiang Liu, Singapore (SG); Wing Kee Damon Wong, Singapore (SG); Masahiro Akiba, Tokyo (JP)

(73) Assignees: AGENCY FOR SCIENCE, TECHNOLOGY AND RESEARCH, Singapore (SG); KABUSHIKI KAISHA TOPCON, Tokyo (JP)

( * ) Notice: Subject to any disclaimer, the term of this patent is extended or adjusted under 35 U.S.C. 154(b) by 48 days.

(21) Appl. No.: 15/528,080

(22) PCT Filed: Nov. 19, 2015

(86) PCT No.: PCT/SG2015/050460
§ 371 (c)(1),
(2) Date: May 18, 2017

(87) PCT Pub. No.: WO2016/080914
PCT Pub. Date: May 26, 2016

(65) Prior Publication Data
US 2017/0319059 A1    Nov. 9, 2017

(30) Foreign Application Priority Data

Nov. 20, 2014  (SG) ............................ 10201407886S (51) Int. Cl.
*G06K 9/00* (2006.01)
*A61B 3/10* (2006.01)
(Continued)

(52) U.S. Cl.
CPC ............ *A61B 3/102* (2013.01); *A61B 3/0025* (2013.01); *G01B 9/02082* (2013.01);
(Continued)

(58) Field of Classification Search
CPC  A61B 3/102; G01B 9/02091; G01B 9/02082; G06T 2207/10101;
(Continued)

(56) References Cited

U.S. PATENT DOCUMENTS

2003/0103212 A1   6/2003  Westphal et al.
2005/0018133 A1*  1/2005  Huang ................... A61B 3/102
                                                       351/205
(Continued)

OTHER PUBLICATIONS

Szkulmowski, Maciej, and Maciej Wojtkowski. "Averaging techniques for OCT imaging." Optics express 21.8 (2013): 9757-9773.*
(Continued)

*Primary Examiner* — Li Liu
(74) *Attorney, Agent, or Firm* — Womble Bond Dickinson (US) LLP (57) ABSTRACT

An optical coherence tomography (OCT) image composed of a plurality of A-scans of a structure is analyzed by defining, for each A-scan, a set of neighboring A-scans surrounding the A-slices scan. Following an optional denoising step, the neighboring A-scans are aligned in the imaging direction, then a matrix X is formed from the aligned A-scans, and matrix completion is performed to obtain a reduced speckle noise image.

11 Claims, 7 Drawing Sheets

(51) Int. Cl.
*G01B 9/02* (2006.01)
*A61B 3/00* (2006.01)
*G06T 5/00* (2006.01)
*G06T 5/50* (2006.01)

(52) U.S. Cl.
CPC ..... *G01B 9/02083* (2013.01); *G01B 9/02091* (2013.01); *G06T 5/002* (2013.01); *G06T 5/50* (2013.01); *G06T 2207/10101* (2013.01)

(58) Field of Classification Search
CPC . G06T 2207/20024; G06T 2207/30041; G06T 5/002; G06T 7/32
See application file for complete search history.

(56) References Cited

U.S. PATENT DOCUMENTS

| | | | |
|---|---|---|---|
| 2012/0099774 A1* | 4/2012 | Akcakaya | G06T 11/008 382/131 |
| 2013/0182930 A1 | 7/2013 | Trzasko et al. | |
| 2014/0126839 A1 | 5/2014 | Qin et al. | |
| 2014/0193095 A1* | 7/2014 | Choe | G06T 5/002 382/274 |
| 2014/0228681 A1* | 8/2014 | Jia | G01B 9/02091 600/425 |
| 2017/0131082 A1* | 5/2017 | Cheng | A61B 3/102 |

OTHER PUBLICATIONS

Rogowska, Jadwiga, and Mark E. Brezinski. "Evaluation of the adaptive speckle suppression filter for coronary optical coherence tomography imaging." IEEE transactions on medical imaging 19.12 (2000): 1261-1266.*

IP Office of Singapore, International Search Report and Written Opinion of the IA for PCT counterpart Application No. PCT/SG2015/050460, 9 pgs., (dated Dec. 1, 2016).

Aja-Fernandez, S., et al. "On the Estimation of the Coefficient of Variation for Anisotropic Diffusion Speckle Filtering," *IEEE Trans. Image Processing*, vol. 15, No. 9, 2006.

Cheng J. et al., "Speckle Reduction in Optical Coherence Tomography by Image Registration and Matrix Completion," International Conference on Medical Image Computing and Computer Assisted Intervention (MICCAI, (Sep. 14-18, 2014), vol. 17, No. Pt 1, pp. 162-169.

Cheng J. et al., "Speckle Reduction in Optical Coherence Tomography by Matrix Completion Using Bilateral Random Projection." Engineering in Medicine and Biology Society (EMBC), 2014 36th Annual International Conference of the IEEE, (Aug. 26-30, 2014), pp. 186-189.

Hendargo H.C. et al., "Automated Non-rigid Registration and Mosaicing for Robust Imaging of Distinct Retinal Capillary Beds Using Speckle Variance Optical Coherence Tomography," *Biomed Opt. Express*, (May 7, 2013), vol. 4, No. 6, pp. 803-821.

Krissian, K. et al., "Oriented Speckle Reducing Anisotropic Diffusion," *IEEE Trans. Image Processing*, vol. 16(5), pp. 1412-1424, 2007.

Kuan, D.T. et al., "Adaptive Noise Smoothing Filter for Images with Signal Dependent Noise," *IEEE Trans. Pat. Anal. Mach. Intell.*, vol. 7, pp. 165-177, 1985.

Lee, J.S., "Speckle Analysis and Smoothing of Synthetic Aperture Radar Images." *Computer Graphics Image Processing*, vol. 17, pp. 24-31, 1981.

Lopes, A. et al., "Adaptive Speckle Filter and Scene Heterogeneity," *IEEE Trans. Geosci. Remote Sens.*, vol. 28, pp. 992-1000, 1900.

Perona, P. et al., Scale-Space and Edge Detection Using Anisotropic Diffusion, *IEEE Trans. Patt. Ana. Mach. Intell.*, vol. 12, pp. 629-639, 1990.

Sander B. et al., "Enhanced Optical Coherence Tomography Imaging by Multiple Scan Averaging," *Br. J. Ophthalmol.*, (Feb. 2005), vol. 89, pp. 207-212.

Yu Y. et al., "Speckle Reducing Anisotropic Diffusion," *IEEE Trans. Image Processing*, (Nov. 2002), vol. 11, No. 11, pp. 1260-1270.

Zhou T. et al., "Randomized low-rank & sparse matrix decomposition in noisy case," *Proceedings of the 28th International Conference on Machine Learning*, (2011), pp. 33-40.

Zhu S. et al., "A New Diamond Search Algorithm for Fast Block-matching motion estimation," *IEEE Trans Image Process*, (Feb. 2000), vol. 9, No. 2, pp. 287-290.

The International Preliminary Report on Patentability and Written Opinion from the International Bureau of WIPO of application PCT/SG2015/050460 dated May 23, 2017, 5 pages.

Supplementary European Search Report for counterpart application No. EP 15 86 0693 completed Mar. 22, 2018, 4 pages.

Rick Ma, et al., "Decomposition Approach for Low-Rank Matrix Completion and Its Applications," IEEE Transactions on Signals Processing, vol. 62, No. 7, Apr. 1, 2014, pp. 1671-1683.

* cited by examiner

Fig. 1

PRIOR ART

Raw Image = Clean Part + Noise Part

SPECKLE REDUCTION IN OPTICAL COHERENCE TOMOGRAPHY IMAGES

FIELD OF THE INVENTION

The present invention relates to methods and systems for processing optical coherence tomography (OCT) images, to form images with reduced speckle.

BACKGROUND OF THE INVENTION

Optical coherence tomography is an optical signal acquisition and processing method. It captures micrometer-resolution, three-dimensional images from within optical scattering media (e.g., biological tissue). The principle of ocular imaging with OCT is based upon measuring the time-delay of the light reflected from each optical interface when a pencil of light (an "A-scan") enters the eye. A series of A-scans across the structure permits a cross-sectional reconstruction of a plane through the anterior or posterior segment of the eye. This is known as a B-scan.

Speckle is problematic for OCT imaging as well as other imaging modalities including synthetic aperture radar (SAR), remote sensing, ultrasound, sonar, etc. In these fields, a substantial amount of signal processing research has been conducted to combat speckle noise, resulting in the development of powerful digital filters for reducing speckle while preserving edge sharpness. Speckle reduction in OCT has been addressed by modifying imaging configurations and through the use of signal processing.

Existing speckle reduction techniques are mainly based on frames using 1) filters such as Lee filter [1], Kuan filter [2], enhanced LEE filter [3]; 2) anisotropic diffusion such as proposed an anisotropic diffusion [4], speckle reduction anisotropic diffusion (SRAD) [5], detail preserving anisotropic diffusion [6] and orientated speckle reduction anisotropic diffusion [7]. These methods were first proposed for radar images and they are applicable for OCT images.

Topcon has developed DRI OCT-1, a swept source OCT for posterior imaging, utilizing a wavelength of 1,050 nm. It has a fast scanning speed of 100,000 A-scans/sec. Utilizing this 1,050 nm wavelength, DRI OCT-1 can penetrate deeper compared to the current conventional OCTs with wavelength in the 850 nm range. Visualizing ocular tissues such as choroid or even sclera, can be done within a very short time. Deep range imaging DRI OCT-1 displays detailed structures of not only retina but choroid and even sclera. With the capability of imaging deeper anatomic structures with less influence in scattering, DRI OCT-1 can visualize the entire tomogram with high sensitivity.

However, in the Topcon DRI OCT-1 swept source OCT, a single frame or slice of the image usually has poor quality due to large speckle noise. Accordingly, conventionally a moving average is computed. For example in the 3D mode with 256 frames, a moving average is computed from 3 to 5 neighboring frames in the DRI OCT-1. Although moving averaging has been shown to be able to reduce speckle noise, the reduction in speckle due to averaging over a small number of neighboring frames is limited. However, if more frames were included in the averaging, blur would appear as a visible artefact, especially in regions where the underlying retinal structures are changing rapidly.

SUMMARY OF THE INVENTION

The present invention aims to provide new and useful methods and systems for analysing an optical coherence tomography (OCT) image composed of a plurality of A-scans, each A-scan being a one-dimensional scan of a structure imaged in a predefined direction.

In general terms, the present invention proposes reconstructing each A-scan from a set of neighbouring A-scans surrounding the A-scan, i.e. the nearest neighbours of the A-scan in a two-dimensional region extending perpendicular to the imaging direction.

Another way of expressing this is that, for a given A-scan, the set of neighbouring scans collectively defines a convex hull which is a cylinder extending in the imaging direction, and the A-scan is a line within the convex hull and encircled by the periphery the convex hull. The A-scan may be a substantially central line within the convex hull. As viewed along the imaging direction the set of neighbouring scans has a two-dimensional profile. The convex hull may for example have a rectangular profile or an elliptical profile.

The A-scans of the neighbourhood are first aligned in the imaging direction, then a matrix X is formed of the aligned A-scans, and matrix completion is performed to obtain a reduced speckle noise image.

The matrix reduction is performed by seeking a second matrix which minimizes a cost function indicative of the difference between the first matrix X and the second matrix, where the second matrix obeys a complexity constraint.

In a first case, the second matrix is a single matrix L, and the complexity constraint is that the second matrix L is constrained to have a rank no higher than a predefined value.

In a second case, the complexity constraint is that, representing the second matrix as the sum of a low rank matrix L and a sparse matrix S, the low rank matrix is constrained to have a rank less than a first predetermined value, and the sparse matrix S is constrained to have a number of non-zero elements less than a second predetermined value.

In either case, the low rank matrix L is a version of the matrix X in which the speckle noise has been reduced, and the column of the low rank matrix L corresponding to the A-scan of X is a low speckle noise reconstruction of the A-scan.

A method which is an embodiment of the method may be carried out by an OCT imaging system, such as the Topcon swept source OCT imaging system, to enhance OCT imaging quality.

One possible specific expression of the present invention is a computer-implemented method of enhancing an optical coherence tomography (OCT) image composed of a plurality of A-scans, each A-scan being indicative of a structure imaged in a predefined direction, the A-scans being grouped as one or more B-scans, the method comprising, for each A-scan:

(a) defining a respective neighbourhood surrounding the A-scan;

(b) aligning the A-scan in the pre-defined direction with other A-scans in the respective neighbourhood;

(c) using the aligned A-scans to form a first matrix X, respective columns of the first matrix being the aligned A-scans; and (d) seeking a second matrix which the minimizes a cost function indicative of the difference between the first matrix X and the second matrix, the second matrix being constrained to obey a complexity constraint.

An enhanced version of the A-scan may be obtained from a column of the second matrix. Alternatively, if the complexity constraint on the second matrix is in the form of a complexity constraint on each of multiple matrix components of the second matrix, then an enhanced version of the A-scan may be obtained from a column of one of the matrix components. In either case, further processing steps may be performed to obtain the enhanced version of the A-scan, such as a filtering step.

The invention may also be expressed in terms of a computer system for performing the method. It may also be expressed as a computer program product (e.g. a tangible data storage device which stores program instructions in non-transitory form) incorporating program instructions which can be run by a processor of a computer system to cause the processor to perform the method.

BRIEF DESCRIPTION OF THE DRAWINGS

An embodiment of the invention will now be described for the sake of example only with reference to the following drawings, in which:

FIG. 8 is composed of FIGS. 8(a)-(f), in which FIGS. 8(a) and (d) show raw OCT data, FIGS. 8(b) and 8(e) show a moving average of the raw data, and FIGS. 8(c) and 8(f) show data obtained by the method of FIG. 1.

DETAILED DESCRIPTION OF THE EMBODIMENTS

Figure 1:
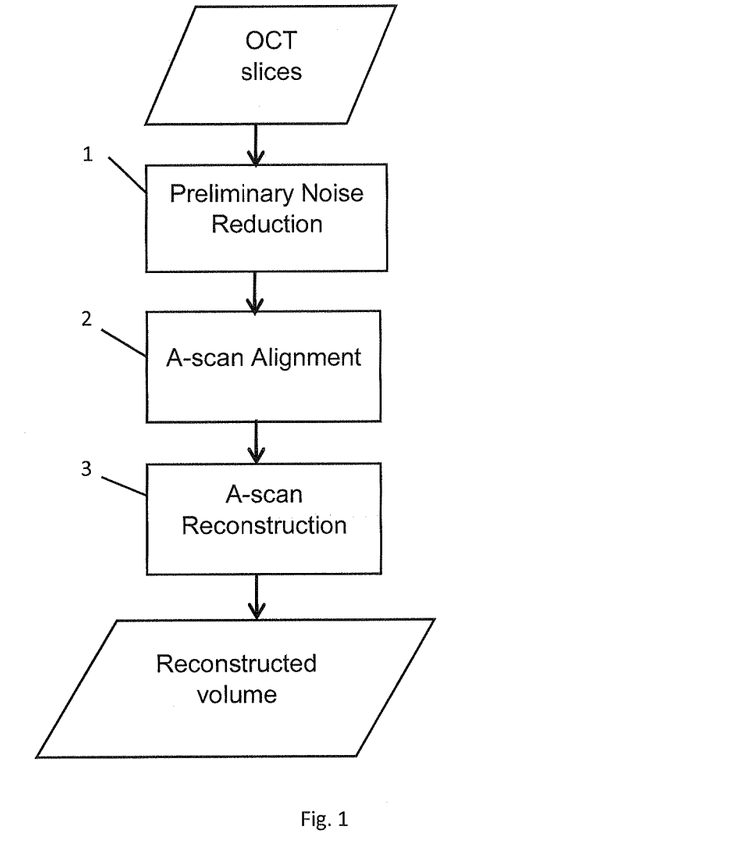
FIG. 1 is a flow chart showing a method which is an embodiment of the invention.
Figure 2:
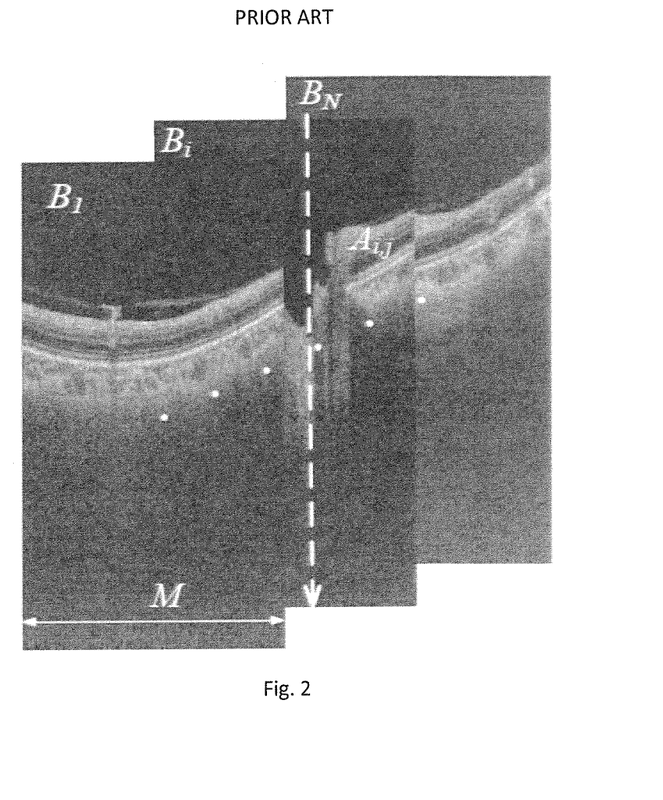
FIG. 2 illustrates OCT images of a three-dimensional volume, the OCT images being N B-scans $B_1, B_2, \ldots, B_N$.

Referring to FIG. 1, a method according to the invention is illustrated. The input to the method is an OCT volume, of the kind which can be produced by a conventional OCT method. The OCT volume is made up of N B-scans (also referred to in the art as "frames" or "slices"), $B_i$ for i=1, 2, ... N, as illustrated in FIG. 2. Each B-scan $B_i$ consists of M A-scans, $A_{i,j}$=1, 2, ..., M, which are each one-dimensional scans formed by imaging the object with a one-dimensional pencil of light extending in the direction which is vertical in FIG. 1. In other words, the OCT volume consists of a set of A-scan lines $A_{i,j}$, i=1, 2, ..., N, j=1, 2, ..., M, where N is the number of B-scans in the volume and M is the number of A-scans in each B-scan.

A basic concept underlying the method of FIG. 1 is to formulate $A_{i,j}$ as a sum of its underlying clean image $l_{i,j}$, and noise $g_{i,j}$, i.e., $$A_{i,j} = l_{i,j} + g_{i,j}$$

The objective is to reconstruct $l_{i,j}$ from $A_{i,j}$. It is impossible to solve this problem without some assumptions about $l_{i,j}$ and $n_{i,j}$, but the embodiment is motivated by the assumption that $l_{i,j}$ is very similar within a small neighborhood. Based on this assumption, we model the neighboring A-scans using similar model.

$$A_{i+p,j+q} = l_{i+p,j+q} + g_{i+p,j+q},$$

where $(p,q) \in \Omega$ and $\Omega$ denotes a "neighborhood" (or "neighbor region"), that is a set of A-scans which are neighbors of, and surround, the A-scan. Thus, the set of A-scans form a two-dimensional array as viewed in the imaging direction.

Figure 3:
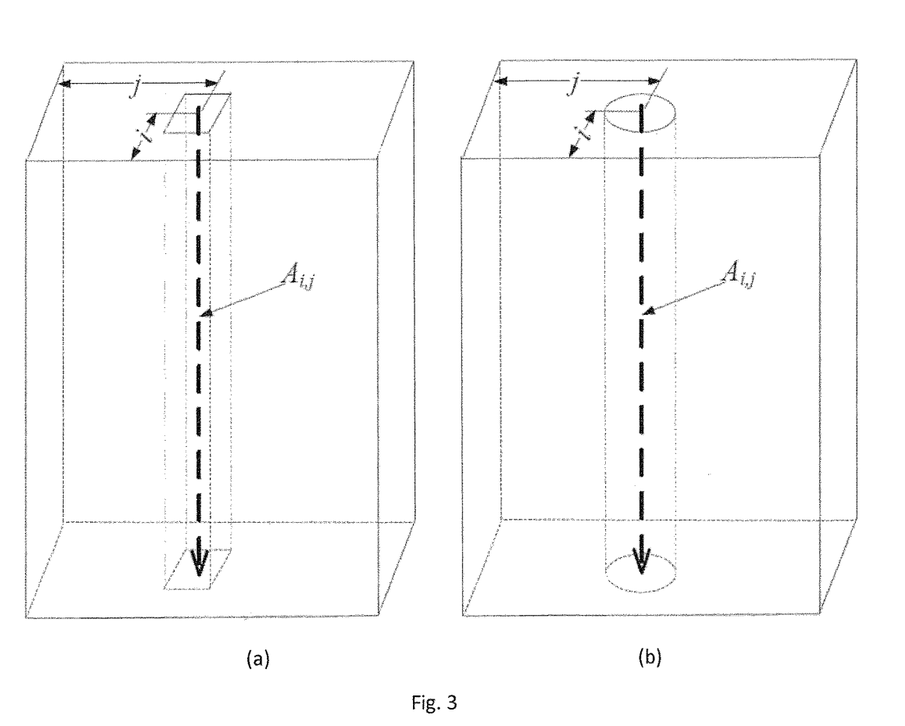
FIG. 3 is composed of FIGS. 3(a) and 3(b), which respectively illustrate two methods of defining a neighbourhood of an A-scan $A_{i,j}$ as (a) a rectangular neighborhood and (b) a circular/elliptical neighborhood.

There are many ways to define the neighbor region. A first possible definition is as the rectangular region $\{(p,q)| -n \le p \le n, -m \le q \le m\}$ as illustrated in FIG. 3(a). An alternative possible definition is as the elliptical region $$\left\{(p, q) \left| \frac{p^2}{n^2} + \frac{q^2}{m|^2} \le 1\right.\right\}$$

as illustrated in FIG. 3(b). If n=m then the neighborhoods are respectively square and circular. In the experiments reported below, the neighborhoods were defined as the rectangular neighborhoods of FIG. 3(a), using n=1 and m=2.

One way to implement this concept would be to define X as the matrix formed by stacking all the A-scans from $\Omega$ as columns, i.e., $X=[A_{i-n,j-m}, \ldots, A_{i+n,j+m}]$, $L=[l_{i-n,j-m}, \ldots, l_{i+n,j+m}]$, $G=[g_{i-n,j-m}, \ldots, g_{i+n,j+m}]$. Each column in L may be assumed to be very similar, so the rank of L is expected to be low, and accordingly the method can use low rank matrix completion to solve L from given X.

Unfortunately, applying the above technique directly to raw OCT volume may lead to some blur of the A-scans due to content changes among neighboring A-scans. In addition, the inevitable eye movement also leads to some misalignment. For this reason, FIG. 1 includes a step 2 of aligning the A-scans, before the A-scan reconstruction by matrix completion is performed in step 3.

Furthermore, the original OCT A-scans are affected by large speckle noise, which make it challenging job to align these A-scans in step 2. Therefore, a pre-processing step 1 is used to reduce the noise before step 2 is carried out.

Many algorithms [1]-[7] can be used for the noise-reduction step 1. We use the SRAD algorithm [5]. SRAD is applied on every scan $B_i$. Specifically, given an intensity image $I_0$ (x, y), the output image I(x, y; t) is evolved according to the PDE:

$$\begin{cases} \frac{\partial I}{\partial t} = div[c(q) \cdot \nabla I] \\ I(t=0) = I_0 \end{cases},$$

where c(q) denotes the diffusion coefficient computed with $$c(q) = 1/(1 + [q^2(x, y; t) - q_0^2(t)]/[q_0^2(t)(1 + q_0^2(t))]) \text{ or}$$

$$c(q) = \exp\{-[q^2(x, y; t) - q_0^2(t)]/[q_0^2(t)(1 + q_0^2(t))]\} \text{ and}$$

$$q(x, y; t) = \sqrt{\frac{(1/2)(|\nabla I|/I)^2 - (1/16)(\nabla^2 I/I)^2}{[1 + (1/4)(\nabla^2 I/I)]^2}}.$$

In the experimental results presented below, the iteration was performed 50 times.

Figure 4:
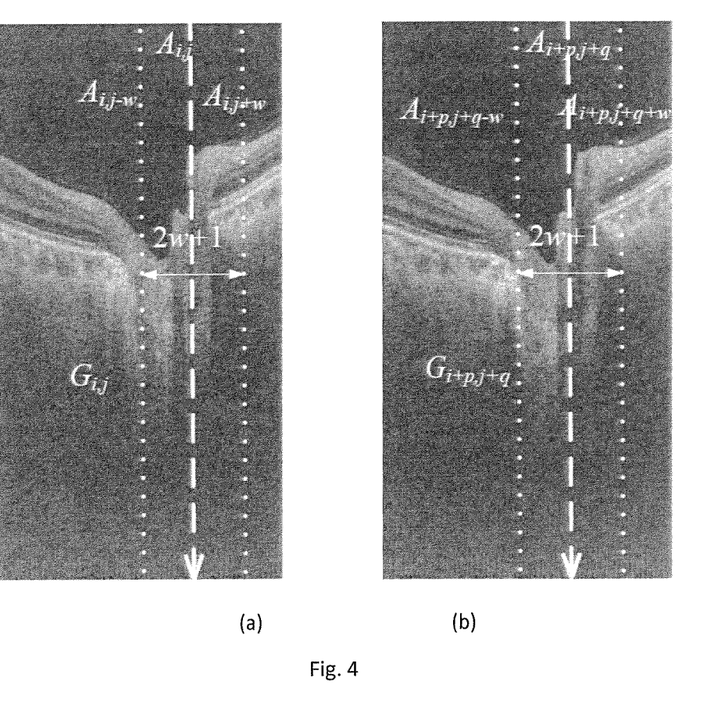
FIG. 4 illustrates an A-scan alignment step of the method of FIG. 1.

In the A-scan alignment step 2, neighboring A-scans $A_{i+p,j+q}$, $(p,q) \in \Omega$ are aligned to $A_{i,j}$ by a vertical translation $\Delta_{p,q}$ (i.e., moving up or down) such that the difference in between is minimized, where $\Omega$ denotes the locations of neighboring A-scans. From our experience, computing the difference from an A-scan alone may lead to a result dominated by local speckle noise. Therefore, we compute the difference between $A_{i,j}$ and $A_{i+p,j+q}$ using their neighboring A-scans as well.

In step 2, for each p and q we define a group ("window") of A-scans centered at $A_{i+p,j+q}$ and $A_{i,j}$, i.e., $G_{i+p,j+q}=[A_{i+p,j+q-w}, A_{i+p,j+q-w+1}, \ldots, A_{i+p,j+q+w}]$ and $G_{i,j}=[A_{i,j-w}, A_{i,j-w+1}, \ldots, A_{i,j+w}]$ where w determines the window size, is used to compute the alignment. We find vertical translation $\Delta_{p,q}$ on $G_{i+p,j+q}$ such that the difference between the translated $G_{i+p,j+q}$ and $G_{i,j}$ is minimized. Many block matching algorithms can be used to find the alignment. In our numerical investigation of the embodiments, we use the diamond search strategy [8] to find the vertical translation because of its efficiency and easy implementation.

We now present two methods by which step 3 can be carried out, i.e. two versions of step 3. A first sub-step of both methods is to combine the aligned A-scans as the columns of the matrix X. That is, $X=[A_{i-n,j-m}, \ldots, A_{i+n,j+m}]$, where the content of the bracket is understood to be the aligned A-scans. Method 1: First, the embodiment decomposes X as a sum of low rank part and noise part, i.e., $$X = L + G, \quad (1)$$

where L is the low rank part with rank $(L) \leq r$, and G is the noise. In the experiments reported below, we set r=2.

The above decomposition is solved by minimizing the decomposition error:

$$\min_L \|X - L\|_F^2, \text{ s.t. rank}(L) \leq r \quad (2)$$

The notation $\|C\|_F$ of any matrix X denotes the Frobenius norm of the matrix (i.e. the Euclidean norm of a vector formed by stacking the columns of the matrix).

The optimization problem above is solved by the bilateral random projections [9] algorithm. The algorithm is summarized as follows:

Algorithm 1 for solving L
Generate a random matrix $A_1$
$A_1 \in R^{D \times r}$; where D is the number of pixels in an A-scan
Compute $\tilde{L} = (XX^T)^q X$; (we use q=2)
$Y_1 = \tilde{L} A_1, A_2 = Y_1$
$Y_2 = \tilde{L}^T Y_1, Y_1 = \tilde{L} Y_2$
Using standard methods, calculate QR decomposition $Y_1 = Q_1 R_1, Y_2 = Q_2 R_2$, where $Q_1$ and $Q_2$ are orthogonal matrices and $R_1$ and $R_2$ are upper triangular matrices;

$$L = Q_1 [R_1 (A_2^T Y_1)^{-1} R_2^T]^{1/(2q+1)} Q_2^T;$$

Method 2: In the second method, the embodiment decomposes the X as a sum of low rank part, sparse part and noise part, i.e., $$X = L + S + G, \quad (3)$$

where L is the low rank part with rank $(L) \leq r$, S is the sparse part with card$(S) \leq k$ and G is the noise. In the experiments reported below, r was equal to 2, and k was set as 30% of the total elements of the matrix S.

The above decomposition is solved by minimizing the decomposition error:

$$\min_{L,S} \|X - L - S\|_F^2, \quad (2)$$
$$\text{s.t. rank}(L) \leq r,$$
$$\text{card}(S) \leq k.$$

The optimization problem above is solved by alternatively solving the following two sub-problems until convergence.

$$\begin{cases} L_t = \arg \min_{\text{rank}(L) \leq r} \|X - L_{t-1} - S_{t-1}\|_F^2 \\ S_t = \arg \min_{\text{card}(S) \leq k} \|X - L_{t-1} - S_{t-1}\|_F^2 \end{cases}$$

The algorithm is summarized as follows:
Algorithm 2 for Solving L
Initialize t:=0; $L_0 = X$; $S_0 = 0$;
While $\|X - L_t - S_t\|_F^2 / \|X\|_F^2 > \varepsilon$, do
t:=t+1;
$\tilde{L} = [(X - S_{t-1})(X - S_{t-1})^T]^q (X - S_{t-1})$;
Generate a random matrix $A_1 \in R^{D \times r}$; here D is the number of pixels in an A-scan.
Compute $Y_1 = \tilde{L} A_1, A_2 = Y_1$;
$Y_2 = \tilde{L}^T Y_1, Y_1 = \tilde{L} Y_2$
Calculate QR decomposition $Y_1 = Q_1 R_1, Y_2 = Q_2 R_2$;
If rank$(A_2^T Y_1) < r$ then r=rank$(A_2^T Y_1)$, go to the first step;
end if;
$L_t = Q_1 [R_1 (A_2^T Y_1)^{-1} R_2^T]^{1/(2q+1)} Q_2^T$;
$S_t = \wp_\Omega (X - L_t)$, $\Omega$ is the nonzero subset of the first k largest entries of $|X - L_t|$; $\wp_\Omega$ is the projection of a matrix to $\Omega$.
End while Note that the term "column" is used here with a meaning which includes also a row of the matrix; in other words, in principle, X could be formed by stacking the aligned A-scans as the rows of X, but then the transpose of X would be applied before the equations are solved in methods 1 and 2.

It can be see that the first method is a special case of the second method with S=0. The main difference is that the second model separates the difference due to content change from the noise.

Although FIG. 1 shows no further processing steps, optionally various filters can be applied on the reconstructed A-scan volumes. Suitable filters include enhanced Lee, adaptive Wiener filters, etc. For example, an adaptive Wiener filter may be used. In addition, a threshold may be applied to assist the de-noising. Mathematically, we apply the following process:

$$L(x, y) = \begin{cases} T_{low} & L(x, y) < T_{low} \\ L(x, y) & T_{low} \leq L(x, y) \leq T_{high} \\ T_{high} & L(x, y) > T_{high} \end{cases}$$

Where $T_{low}$ and $T_{high}$ are two adaptively determined thresholds.

Results

Figure 5:
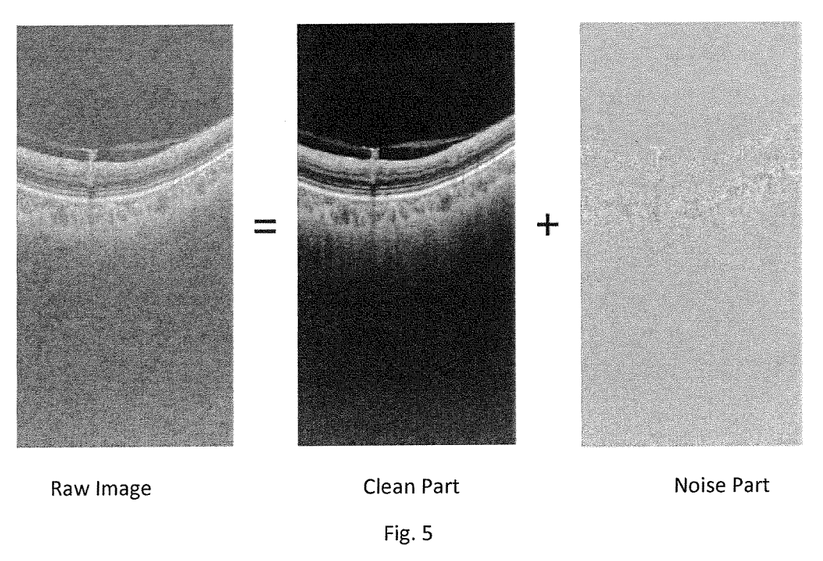
FIG. 5 shows results for image reconstruction using a first version of the method of FIG. 1.

We first present results of the use of the embodiment for the method 1 (i.e. the first variant of step 3). For convenience, we examine the B-scan formed from the reconstructed A-scans. FIG. 5 shows an example of the image recovery including:
  (i) a B-scan of the original data (labelled the "raw image"),
  (ii) the recovered image (labelled the "clean part"). Each column has been obtained from a respective performance of method 1. That is, for a given column of the raw image, a corresponding matrix X is formed. From each X, corresponding matrices L and G are formed by method 1. For each column of the raw image, the corresponding column of the "clean part" image is the column of the corresponding matrix L which has the same position in the corresponding matrix L which the raw image column has in the corresponding matrix X.

(iii) a "noise part" image. For each column of the raw image, the corresponding column of the "noise part" image is the column of the corresponding matrix G which has the same position in the corresponding matrix G which the raw image column has in the corresponding matrix X.

Figure 6:
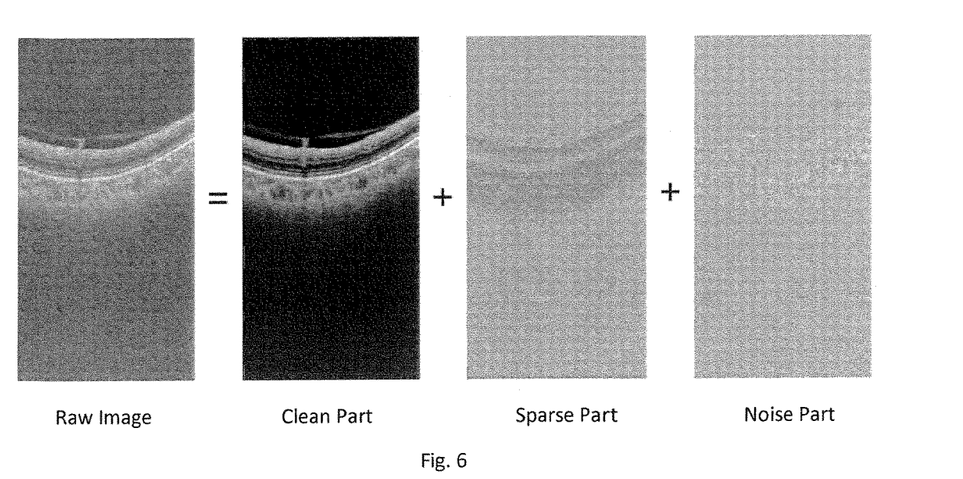
FIG. 6 shows results for image reconstruction using a second version of the method of FIG. 1.

FIG. 6 shows the result when step 3 is performed using the second variant for step 2 (i.e. method 2), modelling X as X=L+S+G.
  (i) a B-scan of the original data (labelled the "raw image"),
  (ii) the recovered image (labelled the "clean part"). Each column has been obtained from a respective performance of method 1. That is, for a given column of the raw image, a corresponding matrix X is formed. From each X, corresponding matrices L, S and G are formed by method 2. For each column of the raw image, the corresponding column of the "clean part" image is the column of the corresponding matrix L which has the same position in the corresponding matrix L which the raw image column has in the corresponding matrix X.
  (iii) a "spare part" image. For each column of the raw image, the corresponding column of the "spare part" image is the column of the corresponding matrix S which has the same position in the corresponding matrix S which the raw image column has in the corresponding matrix X.
  (iv) a "noise part" image. For each column of the raw image, the corresponding column of the "noise part" image is the column of the corresponding matrix G which has the same position in the corresponding matrix G which the raw image column has in the corresponding matrix X.

In both cases, the image L is much sharper than the original image X. Visually, the two results from the two variants of step 3 are very close without much visible difference.

To evaluate the image quality, the contrast to noise ratio (CNR) metric [6] is used. It measures the contrast between a set of regions of interest and a background region.

$$CNR = (1/R)\sum_{1}^{R} (\mu_r - \mu_b) / \sqrt{\sigma_r^2 + \sigma_b^2}$$

where $\mu_r$ and $\sigma_r$ are the mean and variance of all the region of interest, $\mu_b$ and $\sigma_b$ are the mean and variance of the background region. Ten regions of interest from different retinal layers and one background region from each B-scan image were used to compute CNR.

Figure 7:
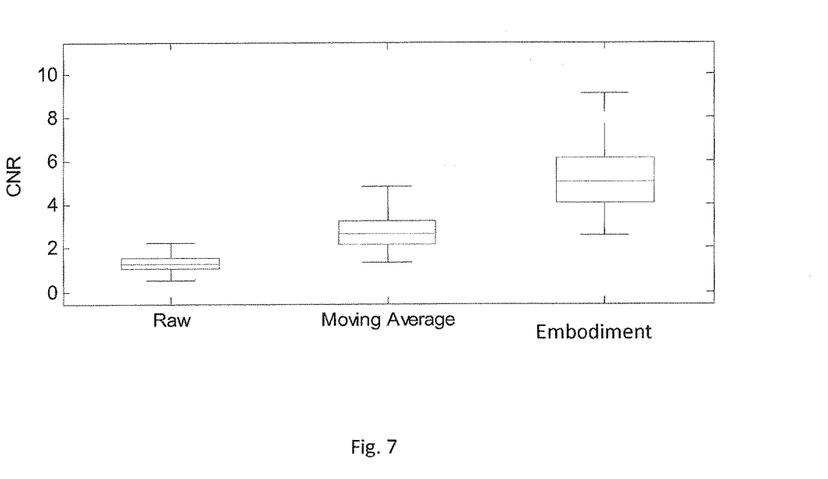
FIG. 7 is a box plot of CNR comparing three methods of speckle reduction.

Two typical OCT volumes with 256 B-scan 992×512 images are used for testing. Table 1 shows the comparison between (i) the raw volume data, (ii) a conventional method using a moving algorithm, and (iii) the embodiment using method 2. As we can observe, the embodiment has a significantly higher CNR. FIG. 7 uses box plot to show the variation of CNRs from different frames.

TABLE 1

Comparison of CNR between the raw data, the conventional moving average speckle reduction algorithm, and an embodiment of the invention

|  | Raw Volume | Moving Average | Embodiment |
|---|---|---|---|
| CNR | 1.30 | 2.73 | 5.26 |

Figure 8:
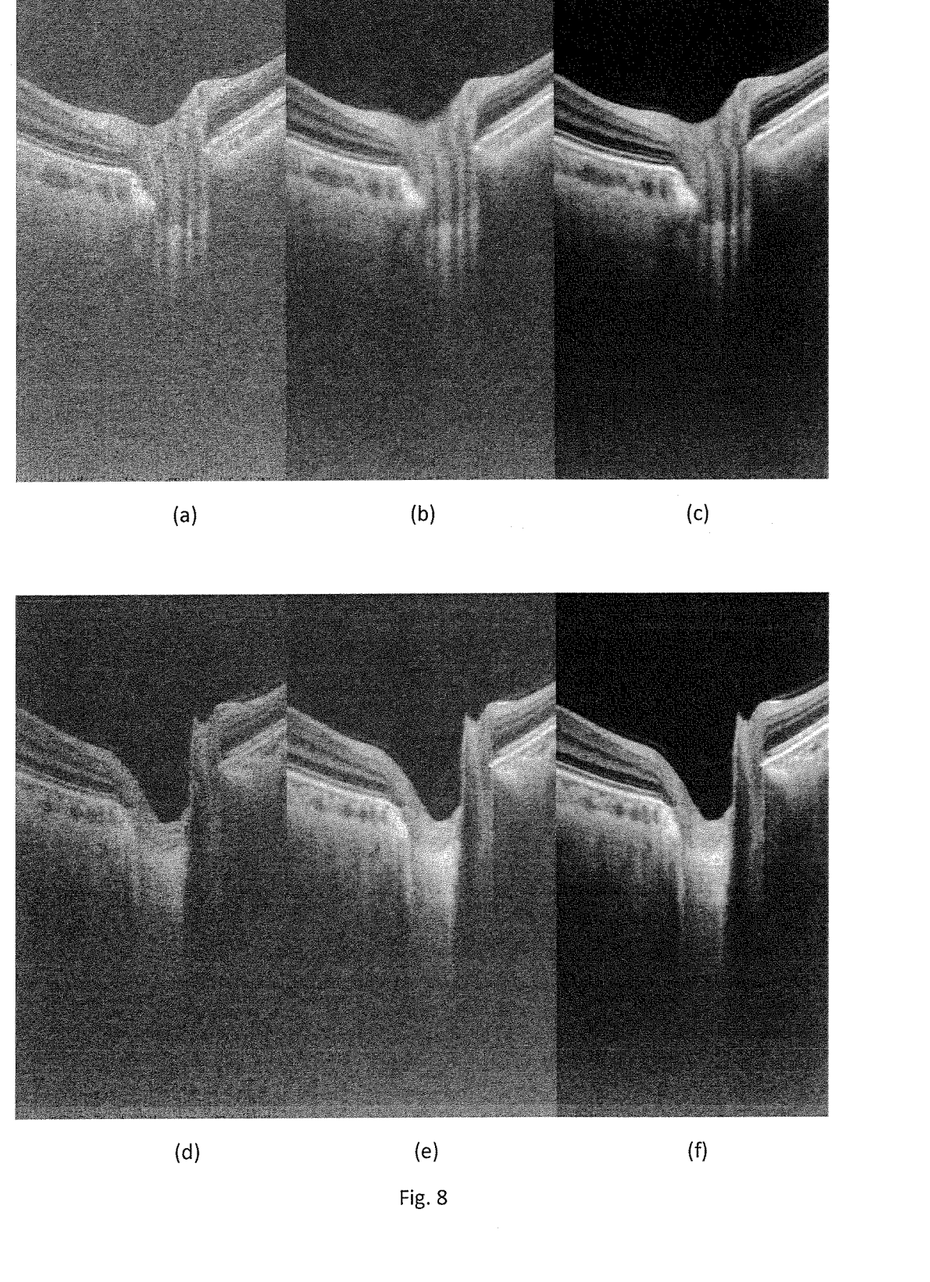

FIG. 8 shows visual difference between the proposed and baseline methods using two examples of raw data (FIGS. 8(a) and 8(d)). The images produced by the moving average method are shown in FIGS. 8(b) and 8(e), while the images produced by an embodiment of the present invention using method 2 are shown in FIGS. 8(c) and 8(d).

Compared to the raw frames and their moving average, the embodiment provides much better volume quality for structure examination. Many more details of the retinal layers and structures such as lamina cribrosa can be examined more comfortably.

Furthermore, the case of performing step 3 by low rank recovery using bilateral random projection is about 20 times faster than traditional algorithms such as robust PCA [8].

The computational process may be implemented using a computer system having a processor and a data storage device which stores program instructions for implementation by a processor, to cause the processor to carry out the method above substantially automatically (that is, without human involvement, except optionally for initiation of the method). The computer system may further comprise a display device having a screen for displaying the result of the method, and/or a printing device for generating a printed form of the result of the method, and/or an interface for transmitting the result of the method electronically. The computer system may be a general purpose computer, which receives the raw images from an interface. Alternatively, it may be part of an OCT imaging device which first captures the images and then processes them using the embodiment.

The resulting images may be used by medical personnel as one tool to perform a diagnosis that a patient is suffering from a condition, and/or to select a medical treatment, such as a surgical procedure, to be carried out on the subject.

REFERENCES

The disclosure of the following references is incorporated herein by reference:
[1] J. S. Lee, "Speckle analysis and smoothing of synthetic aperture radar images," *Computer Graphics Image Processing*, vol. 17, pp. 24-32, 1981.
[2] D. T. Kuan, A. A. Sawchuk, T. C. Strand, and P. Chavel, "Adaptive noise smoothing filter for images with signal dependent noise," *IEEE Trans. Pat. Anal. Mach. Intell.*, vol. 7, pp. 165-177, 1985.
[3] A. Lopes, R. Touzi, and E. Nesby, "Adaptive speckle filter and scene heterogeneity," *IEEE Trans. Geosci. Remote Sens.*, vol. 28, pp. 992-1000, 1990.
[4] P. Perona and J. Malik, Scale-space and edge detection using anisotropic diffusion, IEEE Trans. Patt. Ana. Mach. Intell., vol. 12, pp. 629-639, 1990.
[5] Y. Yu and S. T. Acton, "Speckle reducing anisotropic diffusion," *IEEE Trans. Image Processing*, vol. 11, pp. 1260-1270, 2002.
[6] S. Aja-Fernandez and C. Alberola-López, "On the estimation of the coefficient of variation for anisotropic diffusion speckle filtering," *IEEE Trans. Image Processing*, vol. 15, no. 9, 2006.
[7] K. Krissian, C. F. Westin, R. Kikinis, and K. G. Vosburgh, "Oriented speckle reducing anisotropic diffusion," *IEEE Trans. Image Processing*, vol. 16(5), pp. 1412-1424, 2007.
[8] S. Zhu and K. Ma, "A new diamond search algorithm for fast block-matching motion estimation," *IEEE Trans. Image Processing*, vol. 9, pp. 287-290, 2000.
[9] T. Zhou and D. Tao, "GoDec: Randomized Low-rank & Sparse Matrix Decomposition in Noisy Case", International Conference on Machine Learning, pp. 33-40, 2011

What is claimed is:

1. A computer-implemented method of enhancing an optical coherence tomography (OCT) image composed of a plurality of A-scans, each A-scan being indicative of a structure imaged in a predefined direction, the A-scans being grouped as one or more B-scans, the method comprising, for each A-scan:
    (a) defining a respective neighborhood comprising a set of A-scans surrounding said each A-scan, the set of A-scans forming a two-dimensional as viewed in the predefined direction;
    (b) aligning the set of A-scans in the respective neighborhood to said each A-scan of the respective neighborhood;
    (c) using the aligned A-scans to form a first matrix X, respective columns of the first matrix X being the aligned A-scans; and
    (d) seeking a second matrix which minimizes a cost function indicative of the difference between the first matrix X and the second matrix, the second matrix being constrained to obey a complexity constraint.

2. A method according to claim 1 in which the complexity constraint is that the second matrix is constrained to have a rank no higher than a predefined value.

3. A method according to claim 1 in which the complexity constraint is that, representing the second matrix as the sum of a low rank matrix L and a sparse matrix S, the complexity constraints being that the low rank matrix L is constrained to have a rank less than a first predetermined value, and the sparse matrix S is constrained to have a number of non-zero elements less than a second predetermined value.

4. A method according to claim 1 comprising a prior operation of noise reduction in the plurality of A-scans.

5. A method according to claim 4 in which the noise-reduction is a speckle reduction anisotropic diffusion algorithm.

6. A method according to claim 1 wherein operation (b) is performed by:
    defining a first A-scan group consisting of one or more A-scans including said each A-scan of the respective neighborhood; and
    for each neighbouring A-scan:
        (i) defining a second respective A-scan group, the second respective A-scan group consisting of one or more A-scans including the neighbouring A-scan;
        (ii) seeking a respective translation value which, if the one or more A-scans of the respective second A-scan group are translated in the predefined direction by the translation value, minimises a difference between the first A-scan group and the second A-scan group; and
        (iii) translating the neighbouring A-scan by the respective translation value.

7. A method according to claim 6 in which operation (b) is performed by a block matching algorithm.

8. A method according to claim 7 wherein the block matching algorithm is a diamond search algorithm.

9. A method according to claim 7, wherein the two-dimensional array is a rectangular region or an elliptical region.

10. A computer system comprising a processor and a memory device configured to store program instructions operative, when performed by the processor, to cause the processor to perform a method of enhancing an optical coherence tomography (OCT) image composed of a plurality of A-scans, each A-scan being indicative of a structure imaged in a predefined direction, the A-scans being grouped as one or more B-scans, the method comprising, for each A-scan:
    (a) defining a respective neighborhood comprising a set of A-scans surrounding said each A-scan, the set of A-scans forming a two-dimensional array as viewed in the predefined direction;
    (b) aligning the set of A-scans the respective neighborhood to said each A-scan of the respective neighborhood;
    (c) using the aligned A-scans to form a first matrix X, respective columns of the first matrix X being the aligned A-scans; and
    (d) seeking a second matrix which minimizes a cost function indicative of the difference between the first matrix X and the second matrix, the second matrix being constrained to obey a complexity constraint.

11. A non-transitory computer program product, storing program instructions operative, when performed by a processor, to cause the processor to perform a method of enhancing an optical coherence tomography (OCT) image composed of a plurality of A-scans, each A-scan being indicative of a structure imaged in a predefined direction, the A-scans being grouped as one or more B-scans, the method comprising, for each A-scan:
    (a) defining a respective neighborhood comprising a set of A-scans surrounding said each A-scan, the set of A-scans forming a two-dimensional array as viewed in the predefined direction;
    (b) aligning the set of A-scans in the respective neighborhood to said each A-scan of the respective neighborhood;
    (c) using the aligned A-scans to form a first matrix X, respective columns of the first matrix X being the aligned A-scans; and
    (d) seeking a second matrix which minimizes a cost function indicative of the difference between the first matrix X and the second matrix, the second matrix being constrained to obey a complexity constraint.

* * * * *